United States Patent
Wright et al.

(10) Patent No.: US 8,835,842 B2
(45) Date of Patent: Sep. 16, 2014

(54) SYSTEMS AND METHODS FOR INVESTIGATING A CHARACTERISTIC OF A MATERIAL USING ELECTRON MICROSCOPY

(71) Applicant: EDAX Inc., Mahwah, NJ (US)

(72) Inventors: Stuart I. Wright, Orem, UT (US); Matthew M. Nowell, Riverton, UT (US); Lisa H Chan, Nyack, NY (US); Peter A. de Kloe, Dongen (NL); Tera Lyn Nylese, Pearl River, NY (US)

(73) Assignee: EDAX, Mahwah, NJ (US)

( * ) Notice: Subject to any disclaimer, the term of this patent is extended or adjusted under 35 U.S.C. 154(b) by 0 days.

(21) Appl. No.: 13/746,382

(22) Filed: Jan. 22, 2013

(65) Prior Publication Data

US 2013/0193321 A1 Aug. 1, 2013

Related U.S. Application Data

(60) Provisional application No. 61/592,538, filed on Jan. 30, 2010.

(51) Int. Cl.
*H01J 37/26* (2006.01)
*G01T 1/36* (2006.01)
*H01J 37/29* (2006.01)
*H01J 37/285* (2006.01)
*G01N 23/225* (2006.01)

(52) U.S. Cl.
CPC ......... *H01J 37/26* (2013.01); *H01J 2237/2505* (2013.01); *G01T 1/36* (2013.01); *H01J 37/29* (2013.01); *H01J 37/265* (2013.01); *H01J 2237/28* (2013.01); *H01J 37/285* (2013.01); *G01N 23/2251* (2013.01)
USPC .......................................... 250/305; 250/310

(58) Field of Classification Search
USPC .................................. 250/305, 306, 307, 310
See application file for complete search history.

(56) References Cited

U.S. PATENT DOCUMENTS 3,988,720 A * 10/1976 Ovshinsky .................... 365/113

\* cited by examiner

*Primary Examiner* — Kiet T Nguyen
(74) *Attorney, Agent, or Firm* — Hamilton DeSanctis & Cha (57) ABSTRACT

Various embodiments of the present invention provide systems and methods for determining an characteristic of a material. The characteristics may include, but are not limited to, crystallographic and chemical composition characteristics of a material.

19 Claims, 7 Drawing Sheets

SYSTEMS AND METHODS FOR INVESTIGATING A CHARACTERISTIC OF A MATERIAL USING ELECTRON MICROSCOPY

CROSS REFERENCE TO RELATED APPLICATIONS

The present application claims priority to (is a non-provisional of) Provisional U.S. Pat. App. No. 61/592,538 entitled "TEMPORAL EM SIGNAL TRACKING AND RECOVERY" and filed by Wright et al. on Jan. 30, 2012. The entirety of the aforementioned references is incorporated herein by reference for all purposes.

BACKGROUND OF THE INVENTION

The present inventions are related to systems and methods for determining characteristics of a material. The characteristics may include, but are not limited to, crystallographic and chemical composition characteristics of a material.

Scanning Electron Microscopes (SEM) have been used to investigate characteristics of samples. Use of SEMs to investigate the crystallographic and chemical composition characteristics of a sample suffers from one or more limitations. For example, exposure of a sample to a beam from an SEM can cause instabilities that hamper signal collection. This instability may be the result of beam damage in a beam sensitive sample or due to beam drift. Alternatively, under exposure of a sample to a beam from an SEM can result in insufficient signal to support a desired investigation.

Hence, for at least the aforementioned reasons, there exists a need in the art for advanced systems and methods for investigating samples.

BRIEF SUMMARY OF THE INVENTION

The present inventions are related to systems and methods for determining characteristics of a material. The characteristics may include, but are not limited to, crystallographic and chemical composition characteristics of a material.

Various embodiments of the present invention provide characteristic investigation systems for investigating an characteristic of a material. The systems include: an input device, a beam, and a detector system. The input device is operable to designate at least one location on a sample and a time period, and the beam is operable to impinge on the at least one location on the sample for the time period. The detector system is operable to repeatedly sense signal data resultant from the interaction of the beam and the sample during the time period, and to generate a first image output corresponding to a first duration of exposure of the at least one location of the sample to the beam and a second image output corresponding to a second duration of exposure of the at least one location of the sample to the beam. As used herein, the phrase "image output" is used in its broadest sense to mean any set of data capable of conversion or processing into a graphical representation. Based upon the disclosure provided herein, one of ordinary skill in the art will recognize a variety of image outputs that may be used in relation to different embodiments of the present invention. For example, an image output may be, but is not limited to, a detected X-ray counts verses X-ray energy profile.

This summary provides only a general outline of some embodiments of the invention. The phrases "in one embodiment," "according to one embodiment," "in various embodiments", "in one or more embodiments", "in particular embodiments" and the like generally mean the particular feature, structure, or characteristic following the phrase is included in at least one embodiment of the present invention, and may be included in more than one embodiment of the present invention. Importantly, such phases do not necessarily refer to the same embodiment. Many other embodiments of the invention will become more fully apparent from the following detailed description, the appended claims and the accompanying drawings.

BRIEF DESCRIPTION OF THE DRAWINGS

A further understanding of the various embodiments of the present invention may be realized by reference to the figures which are described in remaining portions of the specification. In the figures, like reference numerals are used throughout several figures to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

The present inventions are related to systems and methods for determining characteristics of a material. The characteristics may include, but are not limited to, crystallographic and chemical composition characteristics of a material.

Various embodiments of the present invention provide characteristic investigation systems for investigating an characteristic of a material. The systems include: an input device, a beam, and a detector system. The input device is operable to designate at least one location on a sample and a time period. The input device may be, but is not limited to, a mouse, or a touch screen. In some particular embodiments, the input device includes a button and the time period corresponds to a period during which the button is pressed. The beam is operable to impinge on the at least one location on the sample for the time period. In some particular embodiments, the beam is an electron beam generated by a scanning electron microscope. The detector system is operable to repeatedly sense signal data resultant from the interaction of the beam and the sample during the time period, and to generate a first image output corresponding to a first duration of exposure of the at least one location of the sample to the beam and a second image output corresponding to a second duration of exposure of the at least one location of the sample to the beam. The detector system may include, but is not limited to, one or more of an X-ray wavelength dispersive spectrometer, an X-ray energy dispersive spectrometer, and an electron backscatter diffraction detector. In some cases, the first duration and the second duration are within the time period.

In some instances of the aforementioned embodiments, the characteristic investigation systems further includes a display system operable to display a graphical representation of a defined region of the sample. In such instances, the at least one location on the sample is included within the defined region. In various embodiments of the present invention, the detector system is a first detector system, and the characteristic investigation system further includes a second detector system operable to sense a portion of the beam reflected off the sample to yield a third image output from which the graphical representation of the defined region is derived. The second detector system may be, but is not limited to, a backscatter detector, a forward scatter detector, or a combination of a backscatter detector and a forward scatter detector. In some cases, the first detector system and the second detector system are implemented as the same detector.

In other instances of the aforementioned embodiments, the graphical representation is a first graphical representation, and the display is further operable to display a second graphical representation of the first image output, and to display a third graphical representation of the second image output in place of the first graphical representation at some time after the second graphical representation is available. In some such cases, the display system is further operable to re-display the first graphical representation in place of the second graphical representation.

In various instances of the aforementioned embodiments, the characteristic investigation system further includes a memory operable to store the first image output and the second image output. In some instances of the aforementioned embodiments, the second image output is the first image output augmented to include an additional sensed signal data resultant from the interaction of the beam and the sample during a period extending between the end of the first duration and a sample time.

In some instances of the aforementioned embodiments, the beam is held fixed for both the first duration and the second duration. In other instances of the aforementioned embodiments, the at least one location includes at least a first location, a second location, a third location, and a fourth location. In some such instances, the beam is moved from the first location to a second location between the first duration and the second duration, and the input device is further operable to designate a beginning point on a path extending from the third location to the fourth location, and an ending point on the path extending from the third location to the fourth location. The first location and the second location are between the beginning point and the ending point, and the characteristic investigation system includes a display operable to display a graphical representation of a cumulative image output that is formed by combining at least the first image output and the second image output.

Other embodiments of the present invention provide methods for material investigation that include: receiving from an input device a designation of at least one location on a sample, and a time period; impinging a beam on the at least one location for the time period; and repeatedly sensing signal data resultant from the interaction of the beam and the sample during the time period; generating a first image output corresponding to a first duration of exposure of the at least one location of the sample to the beam; and generating a second image output corresponding to a second duration of exposure of the at least one location of the sample to the beam.

Yet other embodiments of the present invention provide systems for investigating an characteristic of a material characteristic. Such systems include: an input device, a beam, a sensor, and a display. The input device is operable to designate a path along a surface of a sample within a defined region. The beam is operable to impinge on the surface of the sample along the path. The sensor is operable to repeatedly sense signal data resultant from the interaction of the beam and the sample along the path. The display is operable to display a graphical representation of a cumulative image output that includes a combination of at least a first image output and a second image output. The first image output corresponds to a first location along the path, the second image output corresponds to a second location along the path, and the first location is distinct from the second location.

Figure 1:
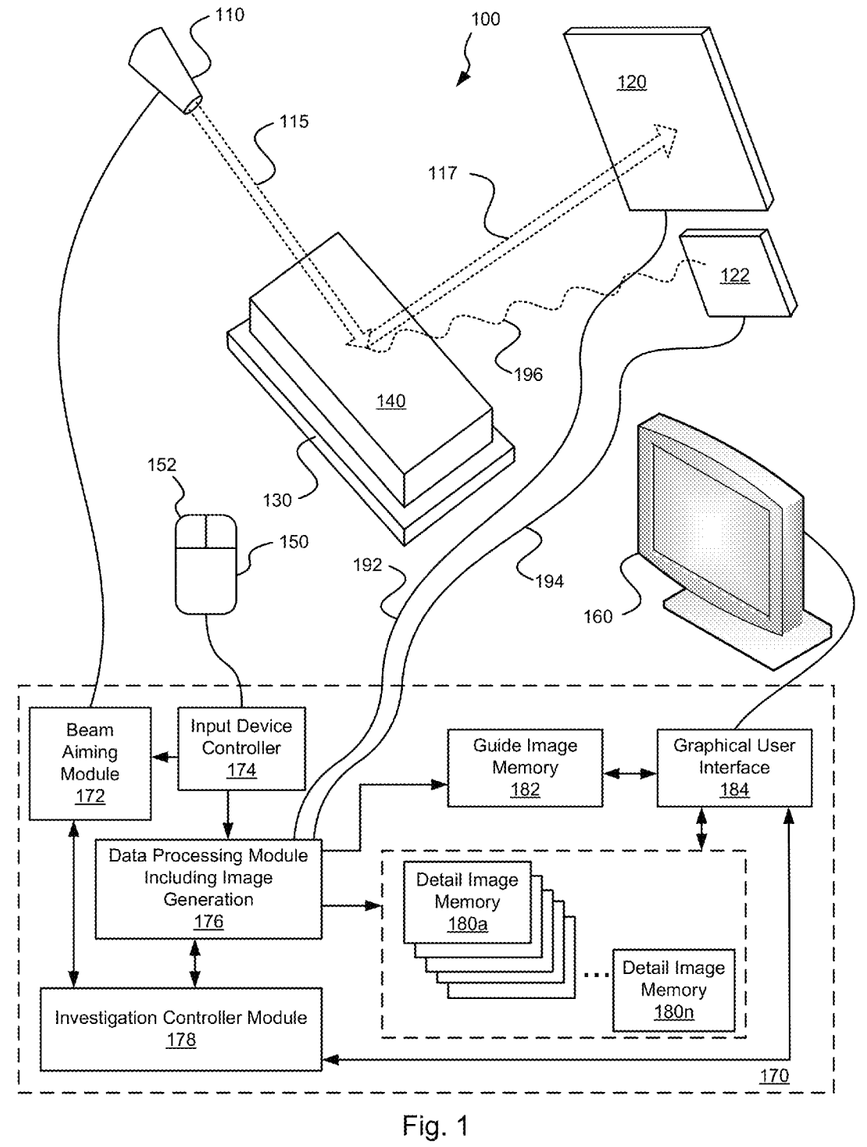
FIG. 1 shows a material investigation system in accordance with various embodiments of the present invention.

Turning to FIG. 1, a material investigation system 100 is shown in accordance with various embodiments of the present invention. Material investigation system 100 includes a radiation source 110 that in this case emits an electron beam 115 toward a material sample 140 that is placed on a carrier 130. In one particular embodiment of the present invention, radiation source 110 is part of a scanning electron microscope. Electron beam 115 reflects off of the material sample as a diffracted electron beam 117 toward a detector 120. Diffracted electron beam 117 creates an electron backscatter diffraction (EBSD) image on a surface of detector 120 that is transferred to a data processing module 176 including image generation. Of note, detector 120 may be replaced by a number of different sensors as are known in the art including, but not limited to, a forward scatter detector. In some cases, detector 120 may be a combination of one or more sensors. Based upon the disclosure provided herein, one of ordinary skill in the art will recognize a variety of sensors or combinations of sensors that may be utilized in accordance with different embodiments of the present invention. In addition, the interaction of electron beam 115 results in the generation of signal data 196 that is sensed by a detector 122. Signal data may be, but is not limited to, an X-ray or a diffracted portion of electron beam 115. In some cases, detector 122 may be, but is not limited to, an X-ray wavelength dispersive spectrometer, or an X-ray energy dispersive spectrometer, or an electron backscatter diffraction detector. In various embodiments of the present invention, detector 120 and detector 122 are implemented as two distinct detectors. In other cases, detector 120 and detector 122 may be implemented as the same detector or as two distinct detectors in the same package. Based upon the disclosure provided herein, one of ordinary skill in the art will recognize a variety of sensors or combinations of sensors that may be utilized in accordance with different embodiments of the present invention to perform the functions of detector 120 and/or detector 122.

Material sample 140 may be any material known in the art. In some particular cases, material sample 140 is a crystalline or polycrystalline material. As an example, material sample 140 may be magnesium or some alloy thereof, or a single crystal silicon sample. Based upon the disclosure provided herein, one of ordinary skill in the art will recognize a variety of materials that may be examined using embodiments of the present invention. Material sample 140 may be placed in a highly-tilted (e.g., approximately seventy degrees) orientation relative to electron beam 115.

Material investigation system 100 further includes an input device 150, a display 160, and a processing device 170. Input device 150 may be any input device known in the art that is capable of indicating a time period and a location. In one particular embodiment of the present invention, input device 150 is a mouse with a button 152. In one such case, the time period is generated to correspond to a duration which button 152 is pressed, and the location is generated by moving the mouse. Alternatively, a touch screen device may be used as input device 150. In such a case, the touch screen may designate location by touching a corresponding location on the touch screen, and time period may be generated to correspond to a duration at which a defined location on the touch screen is continuously touched. Based upon the disclosure provided herein, one of ordinary skill in the art will recognize a variety of input devices that may be used in relation to different embodiments of the present invention. Of note, detectors 120, 122, display 160, input device 150, and radiation source 110 may share the same processing device, use separate processing devices, or may use a combination of separate and shared processing devices. Further, each detector 120, 122 may be associated with its own display or may share a common display.

Processing device 170 includes a beam aiming module 172, an input device controller 174, a data processing module 176 including image generation capability, an investigation controller module 178, a detail image memory 180, a guide image memory 182, and a graphical user interface 184. In some embodiments of the present invention, processing device 170 is a general purpose computer executing processing instructions. In other embodiments of the present invention, processing device 170 is a circuit tailored to perform the operations of material investigation system 100. In yet other embodiments of the present invention, processing device 170 is a combination of a general purpose computer and circuitry tailored to perform the operations of material investigation system 100. Investigation controller module 178 is operable to control application of beam 115 and updates to display 160 through various phases of an investigation.

Beam aiming module 172 is operable to control the location to which radiation source 110 directs beam 115. Beam aiming module 172 relies on instructions from investigation controller module 178 and input device controller to properly direct beam 115. As an example, in one phase of using material investigation system 100, beam aiming module 172 directs radiation source 110 to scan across a defined grid of material sample 140. In a later phase, beam aiming module 172 directs radiation source 110 to a particular location within the defined grid for a time period. The location and the time period are provided by input device controller 174 to beam aiming module 172. As another example, in the later phase, beam aiming module 172 directs radiation source 110 along a path within the defined grid where the path is indicated by the input device.

Input device controller 174 is operable to generate control signals based upon one or more signals received from input device 150. As one example, input device controller 174 generates a time period based upon a length of time that button 152 is pressed, and a location based upon movement of input device 150. In some cases, the location is a fixed location. In other cases, the location is a number of positions along a path.

Guide image memory 182 is operable to store a guide image output corresponding to a map covering a defined region of material sample 140. The stored guide image output may be developed by scanning beam 115 over a defined grid and sensing diffracted electron beam 117 by detector 120. In turn, detector 120 provides signal data 192 to data processing module 176 that generates the guide image output corresponding to a map of the defined region of material sample 140. This guide image output may be accessed by graphical user interface 184 where it is converted to a graphical representation of the defined region displayable by display 160.

Detail image memory 180 is operable to store a number of detailed image outputs corresponding to either one particular location within the defined region of material sample 140 for different exposure durations, or for multiple locations along a path traversing the defined region of material sample 140. In the case of multiple detailed image outputs of the particular location for differing exposure durations, the stored detailed image outputs may be generated by directing beam 115 at a particular location on material sample 140 and sensing signal data 196 by detector 122. In turn, detector 122 provides signal data 194 to data processing module 176 that generates a detailed image output corresponding to the particular location on material sample 140 for a given exposure period. Multiple detailed image outputs are generated for the particular location on material sample 140, but at differing durations of exposure of material sample 140 to beam 115. The difference between exposure lengths of two successive detailed image outputs may be controlled by investigation controller module 178. In some cases, this difference corresponds to a rate at which detector 122 can produce distinct sets of signal data 194 and/or the rate at which data processing module 176 can process signal data 194. Alternatively, in the case of multiple detailed image outputs along a path traversing the defined region of material sample 140, the stored detailed image outputs may be generated by directing beam 115 along the path traversing the defined region across material sample 140 and sensing signal data 196 by detector 122. In turn, detector 122 provides signal data 194 to data processing module 176 that generates a detailed image output corresponding to the particular location on material sample 140 for successive points along the path. Multiple detailed image outputs are generated corresponding to respective locations along the path traversing material sample 140. The difference between successive locations along the path at which detailed image outputs are generated may be controlled by investigation controller module 178. In some cases, this difference corresponds to a rate at which detector 122 can produce distinct sets of signal data 194 and/or the rate at which data processing module 176 can process signal data 194. The detailed image outputs may be accessed by graphical user interface 184 where they are converted to graphical representations of the particular location for the respective durations displayable by display 160.

Figure 2:
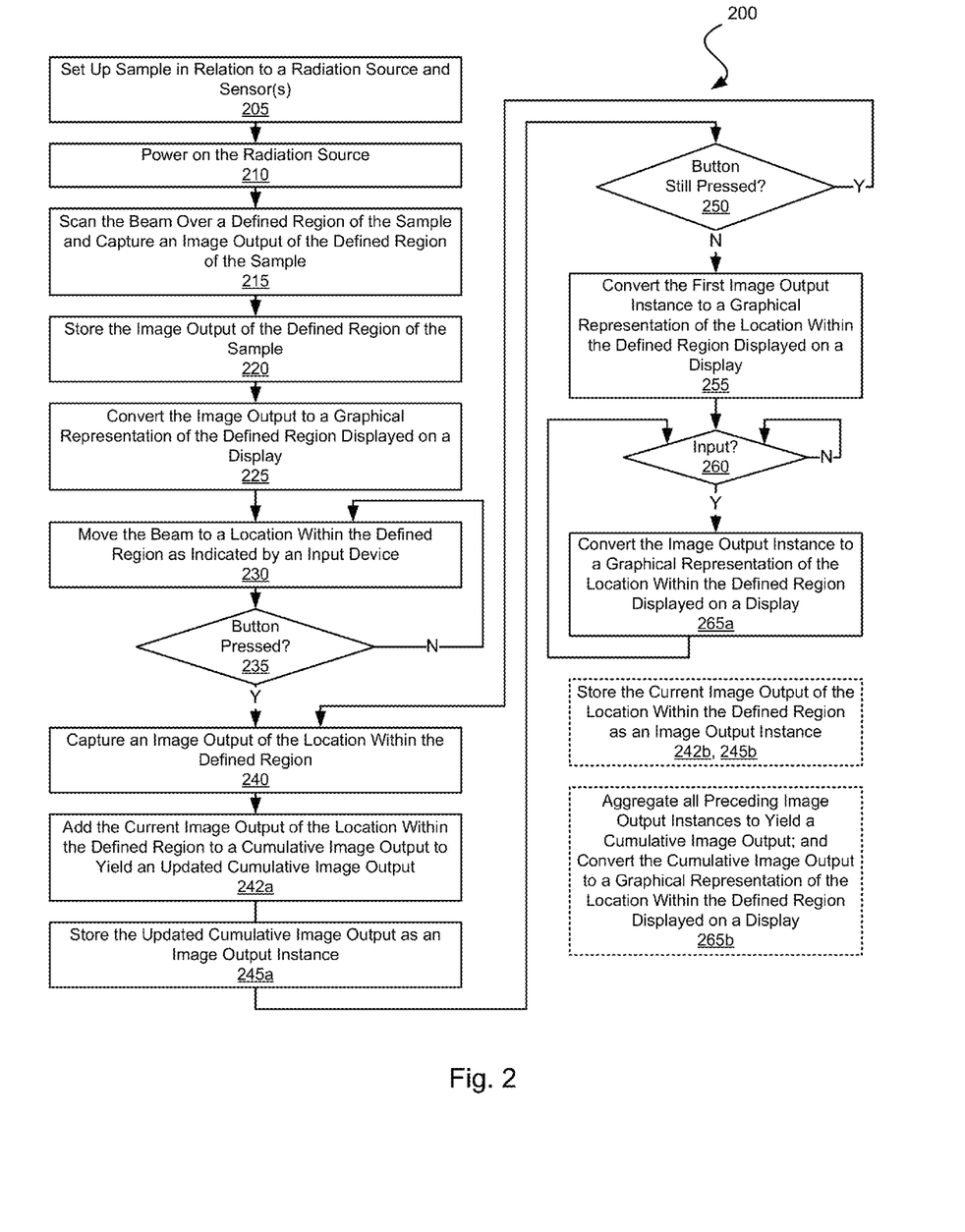
FIG. 2 is a flow diagram showing a method in accordance with some embodiments of the present for investigating a structural characteristic of a sample.
Figure 3:
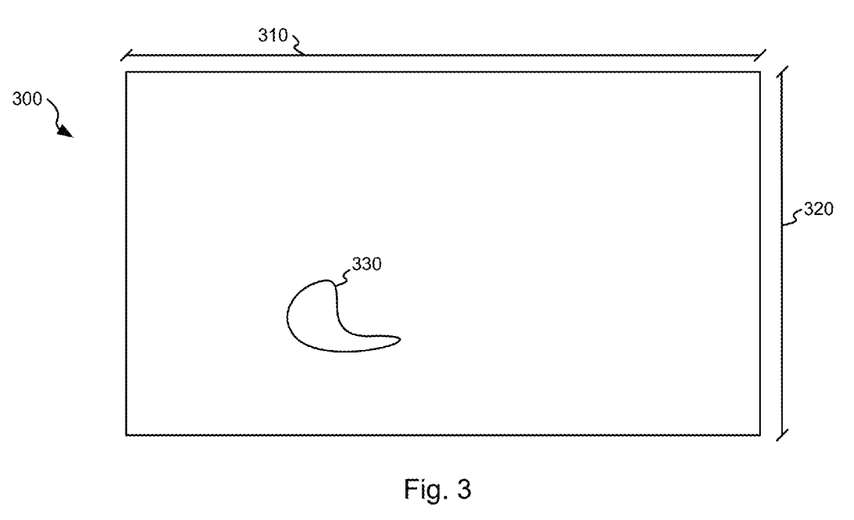
FIG. 3 graphically represents a defined region including a structure to be investigated that may result from use of one or more embodiments of the present invention.

Turning to FIG. 2, a flow diagram 200 shows a method in accordance with some embodiments of the present for investigating a structural characteristic of a sample. Following flow diagram 200, a sample is set up in relation to a radiation source and one or more sensors (block 205). This may include, for example, placing the sample material on a carrier apparatus such that radiation emitted from a radiation source is directed toward the surface of the sample material at a desired incidence angle. The radiation source is then turned on such that a beam emitted from the radiation source impacts the surface of the sample material (block 210). The beam is then scanned over a defined region of the sample, and an image output corresponding to the defined region of the sample is captured (block 215). As used herein, the term "capture" or "captured" are used in their broadest sense to mean sensing or detecting an input and providing a corresponding output at least temporarily. This image output of the defined region includes data that is capable of processing to produce a graphical representation of the defined region. This image output is then stored (block 220), and converted to a graphical representation of the defined region displayed on a display (block 225). This image output of the defined region may be captured using a first detector, and stored to a guide image memory. Turning to FIG. 3, an example graphic of a defined region 300 including a structure 330 to be investigated is shown that may result from use of one or more embodiments of the present invention. As shown, defined region 300 has a width 310 and a height 320.

Figure 4:
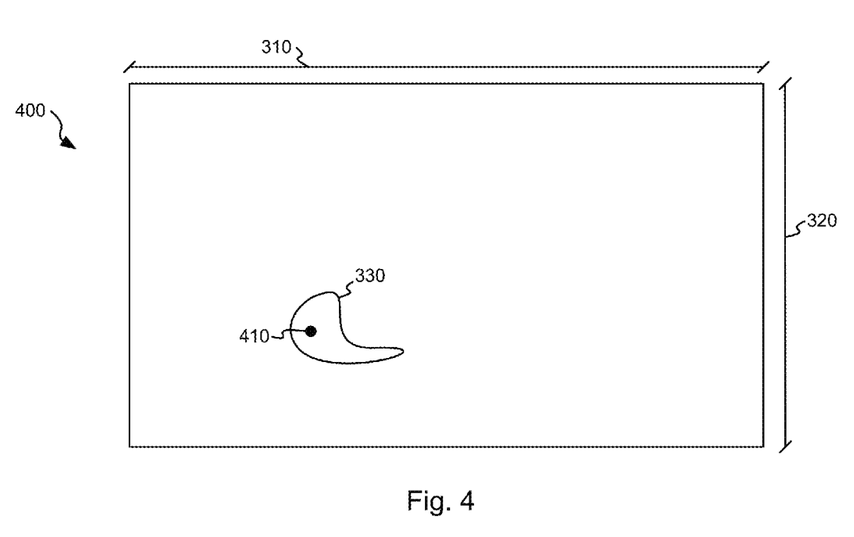
FIG. 4 shows the graphic of FIG. 3 augmented to include a portion of the structure designated by an input device.

Returning to FIG. 2, the beam is moved to a specific location within the defined region as indicated by an input device (block 230). Turning to FIG. 4, defined region 300 is shown in which the input device has been manipulated to point at a specific location 410. Specific location 410 is within the boundaries of structure 330. Returning to FIG. 2, it is determined whether the button of the input device is pressed (block 235). It should be noted that in some cases an input device that does not include a button is used. In such a case, a proxy for a button press may be used. For example, where a touch screen is used, touching the screen at a defined location may be used as a proxy for a button press. Where the button is not pressed (block 235), the beam is moved again to a location within the defined region when the input device indicates a change in location (block 230). Of note the duration of a button press may be captured or generated in a number of other ways including, but not limited to, one press to start a timer and a second press to end the timer with the duration corresponding to the timer. Based upon the disclosure provided herein, one of ordinary skill in the art will recognize a variety of approaches for setting a time period based using an input device.

Alternatively, where the button is pressed (block 235), an image output corresponding to the specific location within the defined region is captured (block 240). This image output of the specific location may be captured using a second detector, and stored to a detailed image memory. The image output (the current instance) is added to a cumulative image output to yield an updated cumulative image output (block 242*a*). For the first image output the cumulative image output is zero, and therefore the updated cumulative image output is equal to the first image output. The updated cumulative image is stored as an image output instance (block 245*a*). The updated cumulative image output represents an image output after exposure of the material sample to the beam for a given duration. This image output instance may be stored to detail image memory 180. As an alternative, non-cumulative image outputs are stored to memory (block 242*b*, 245*b* shown in dashed lines indicating an alternative), and the accumulation is done later (i.e., block 265).

It is then determined whether the button is still pressed (block 250). Where the button is still pressed (block 250), the processes of blocks 240, 242, 245 are repeated again for the same location. Each repetition results in an updated cumulative image output representing an image output after exposure of the material sample to the beam for successively greater durations where cumulative image outputs are stored, or a new image output corresponding to an exposure duration between the exposure time up to capture of a preceding image output and the exposure time up to capture of the succeeding image output.

Where, on the other hand, the button is no longer pressed, the first image output instance from the specific location within the defined region is converted to a graphical representation of the location with the defined region displayed on a display (block 255). The first image output instance is the previously stored image output instance corresponding to the first duration. It is then determined whether input from the input device is received indicating another image output instance (i.e., a different exposure of the sample material to the radiation beam) (block 260). This input may be a forward input causing the display to scroll forward through the image output instances, or a backward input causing the display to scroll backward through the image output instances. Where an input is received, the image output instance indicated by the input is converted to a graphical representation of the location with the defined region displayed on a display (block 265*a*) where the image output instances were previously accumulated (block 242*a*, 245*a*), or all image output instances preceding and including the selected image output instance are aggregated to yield a cumulative image output, and the cumulative image output is converted to a graphical representation of the location with the defined region displayed on a display (block 265*b* shown in dashed lines indicating an alternative).

Figure 5:
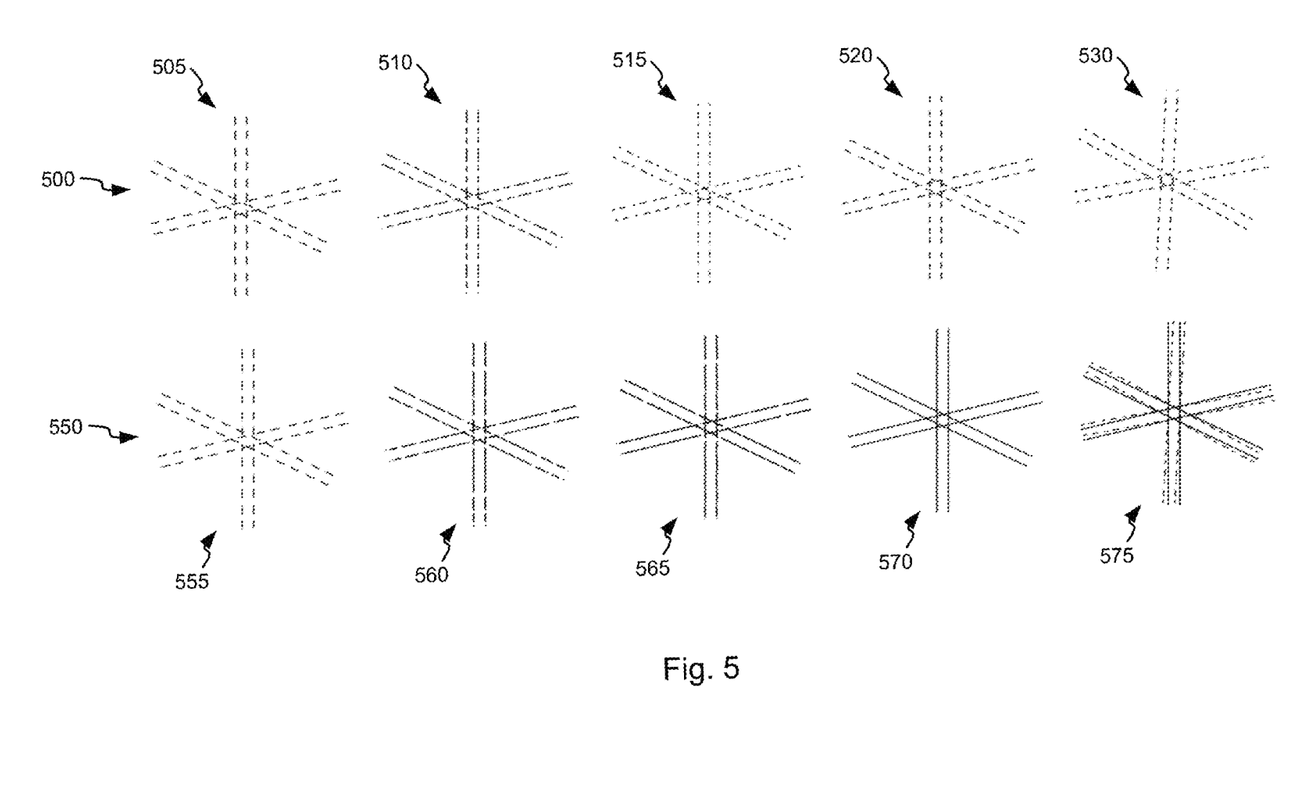
FIG. 5 graphically represents a number of image outputs corresponding to different exposures or different locations along a path, and the same number of cumulative image outputs corresponding to different exposures or different locations along a path that may be generated in accordance with one or more embodiments of the present invention.

This click and dwell approach allows a user to control the time period over which beam 115 impinges on material sample 140, and to generate a number of cumulative images during the time period. Turning to FIG. 5, a graphical representation 500 of a number of image outputs corresponding to different exposures or different locations along a path, and the same number of cumulative image outputs corresponding to different exposures or different locations along a path that may be generated using the system of FIG. 1 and/or the processes of FIG. 2 or FIG. 6 (discussed below) in accordance with one or more embodiments of the present invention are shown. Graphical representation 500 includes a first row 500 including an first image output instance 505 generated at a first exposure duration (i.e., at a time period $T_1$), a second image output instance 510 generated after a second exposure duration (i.e., at a time period $T_2$), a third image output instance 515 generated after a third exposure duration (i.e., at a time period $T_3$), a fourth image output instance 520 generated after a fourth exposure duration (i.e., at a time period $T_4$), and a fifth image output instance 530 generated after a fifth exposure duration (i.e., at a time period $T_5$) ($T_5 > T_4 > T_3 > T_2 > T_1$). These correspond to image instances captured while the button is pressed (block 235 above), or along a path as discussed below in relation to FIG. 6. A second row 550 shows a cumulative image output available after each of the aforementioned exposures. In particular, second row 550 shows: a cumulative image output 555 which is an accumulation of first image output instance 505; a cumulative image output 560 which is an accumulation of first image output instance 505 and second image output instance 510; a cumulative image output 565 which is an accumulation of first image output instance 505, second image output instance 510, and third image instance output 515; a cumulative image output 570 which is an accumulation of first image output instance 505, second image output instance 510, third image output instance 515, and fourth image instance output 520, and a cumulative image output 575 which is an accumulation of first image output instance 505, second image output instance 510, third image output instance 515, fourth image instance output 520, and fifth image instance output 530. Of note, fifth image instance output 530 occurs after a beam drift in which case alignment with previous image instance outputs is skewed. This undermines the fidelity of cumulative image output 575 when compared with the fidelity of cumulative image output 570. Using the approaches discussed in relation to FIG. 2 or FIG. 6, a user may graphically scroll through the resulting image outputs to select an image output that offers sufficient exposure without exhibiting the instability that can occur due to over exposure to the beam. The image output that could be selected would be the image output generated just before the signal starts to degrade due to over exposure (e.g., cumulative image output 570). Subsequent processing on the accumulated signals represented by the selected image output may be performed. For example, an image pattern could be indexed to obtain the crystallographic orientation, and/or an X-ray energy dispersive spectrum or an X-ray wavelength dispersive spectrum may be quantified to determine the chemical composition at the point of interest in the material sample. Of note, beam damage would result in increased noise in the pattern which is not shown in FIG. 5.

Figure 6:
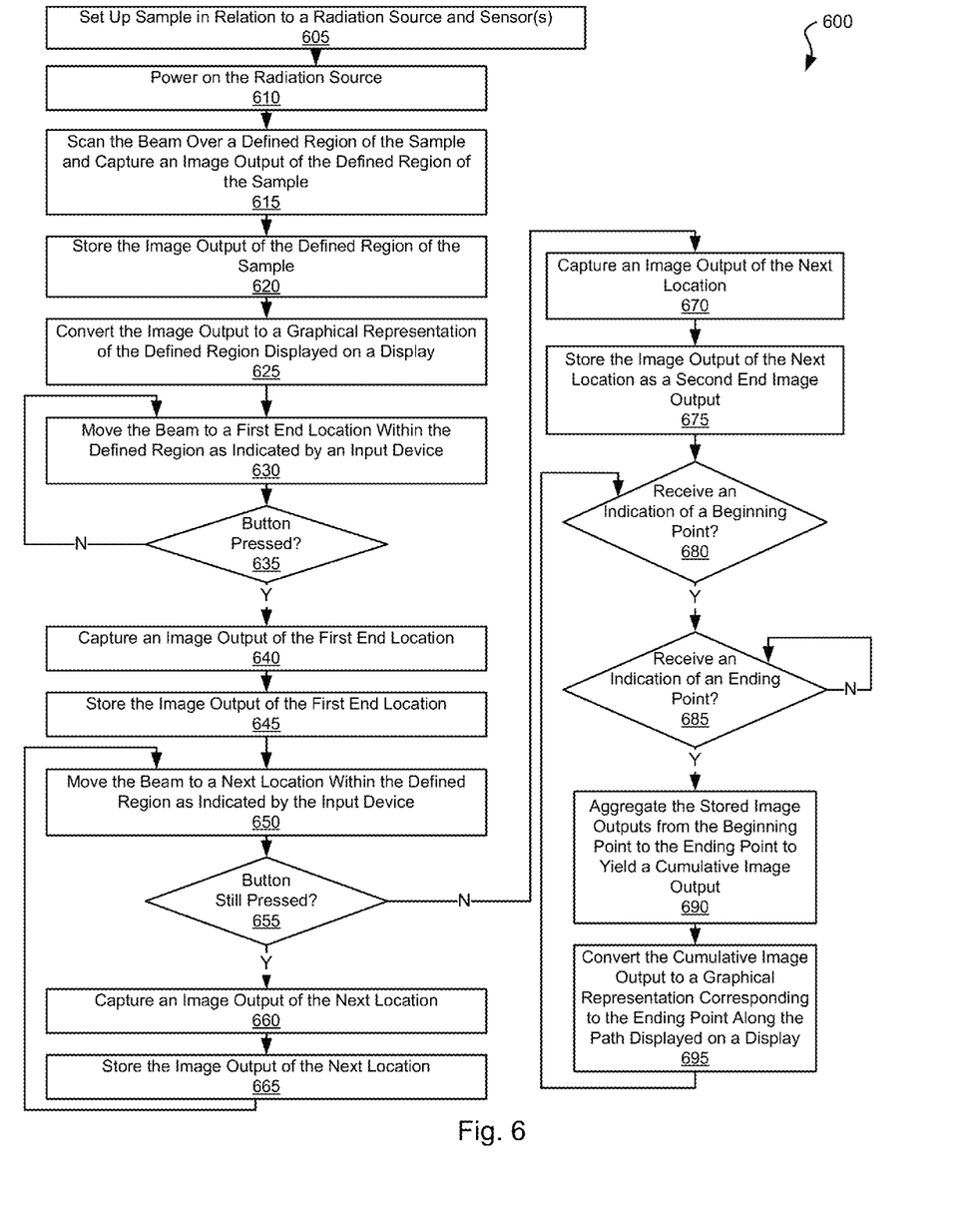
FIG. 6 is a flow diagram showing another method in accordance with other embodiments of the present for investigating a structural characteristic of a sample.
Figure 7:
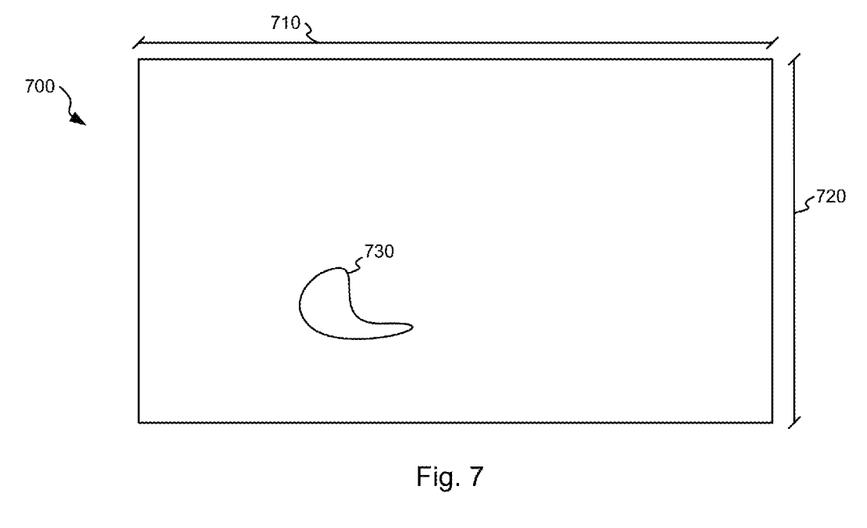
FIG. 7 is an example graphic of a defined region including a structure to be investigated that may result from use of one or more embodiments of the present invention.

Turning to FIG. 6, a flow diagram 600 shows another method in accordance with other embodiments of the present for investigating a structural characteristic of a sample. Following flow diagram 600, a sample is set up in relation to a radiation source and one or more detectors (block 605). This may include, for example, placing the sample material on a carrier apparatus such that radiation emitted from a radiation source is directed toward the surface of the sample material at a desired incidence angle. The radiation source is then turned on such that a beam emitted from the radiation source impacts the surface of the sample material (block 610). The beam is then scanned over a defined region of the sample, and an image output of the defined region of the sample is captured (block 615). This capture includes sensing diffracted electron beam 117 that by detector 120. This image output of the defined region is then stored (block 620), and converted to a graphical representation of the defined region displayed on a display (block 625). This image output of the defined region may be stored to guide image memory 182. Turning to FIG. 7, an example graphic of a defined region 700 including a structure 730 to be investigated is shown that may result from use of one or more embodiments of the present invention. As shown, defined region 700 has a width 710 and a height 720.

Returning to FIG. 6, the beam is moved to a first end location within the defined region as indicated by an input device (block 630). It is determined whether the button of the input device is pressed (block 635). Again, it should be noted that in some cases an input device that does not include a button is used. In such a case, a proxy for a button press may be used. For example, where a touch screen is used, touching the screen at a defined location may be used as a proxy for a button press. Where the button is not pressed (block 635), the beam is moved again to a new first end location within the defined region when the input device indicates a change in location (block 630).

Alternatively, where the button is pressed (block 635), an image output of the material sample at the first end location is captured (block 640). This capture includes sensing signal data 196 that by detector 122. The captured image output is stored as a first end location (block 645). This image output may be stored to detail image memory 180.

Figure 8:
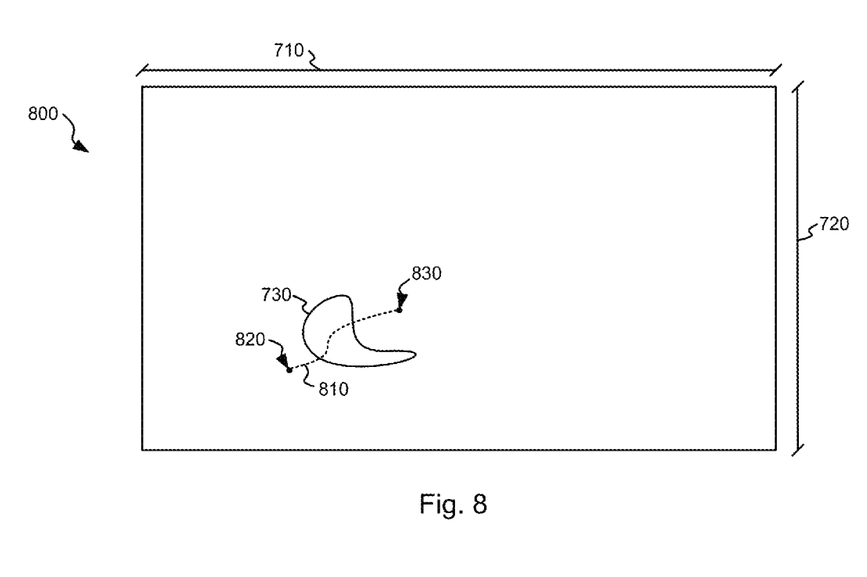
FIG. 8 shows the graphic of FIG. 7 augmented to include a path designated by an input device along which repeated image output generation is applied in accordance with one or more embodiments of the present invention.

In addition, the beam is moved to a next location within the defined region as indicated by the input device (block 650). It is determined whether the button is still pressed (block 655). Where the button is still pressed (block 655), an image output is captured that corresponds to the material sample at the next location (block 660) and the captured image output is stored as a next location image output (block 665). This process of moving the beam to a next location along the path, capturing and storing an image outputs (blocks 650-665) is repeated as long as the button is pressed. This results in a series of image outputs corresponding to different locations along the path. An example graphical representation of such image outputs is set forth in first row 500 of FIG. 5 discussed above. Once the button is no longer pressed (block 655), an image output of the material sample at the next location is captured (block 670) and stored to the memory as an image output corresponding to a second end location (block 675). Turning to FIG. 8, a path 810 from a first end location 820 traverses structure 730 to a second end location 830. Path 810 represents the locations traversed using the input device while the button is pressed between first end location 820 and second end location 830.

Figure 9:
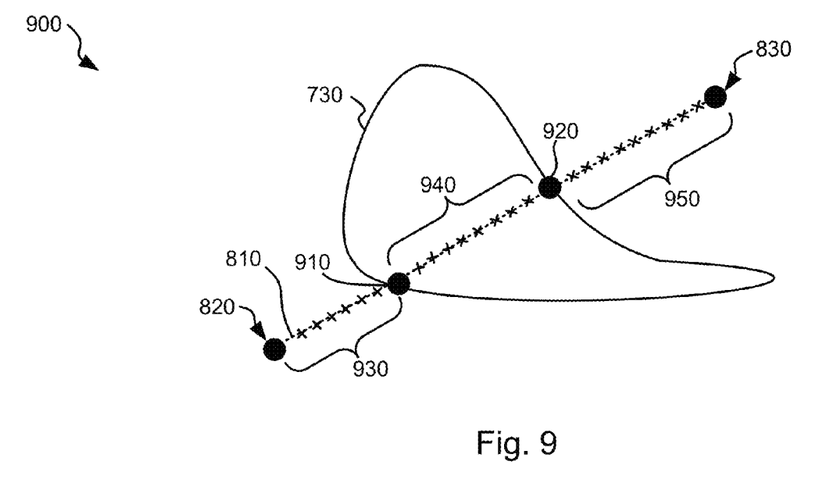
FIG. 9 shows detail of the structure to be investigated including the path along which repeated image output generation is applied augmented to include a beginning point and an ending point designated by the input device.

Returning to FIG. 6, it is determined whether an indication of a beginning point is received (block 680). This beginning point may be received from the input device by moving the input device to a desired location and pressing the button. Based upon the disclosure provided herein, one or ordinary skill in the art will recognize a variety of mechanisms that may be used in relation to different embodiments of the present invention for indicating a beginning point. Once a beginning point has been received (block 680), it is determined whether an indication of an ending point is received (block 685). This may be done using a similar mechanism to that used to indicate the beginning point. Turning to FIG. 9, detail 900 of structure 730 including path 810, a first end location 820, a second end location 830, a beginning point 910, and an ending point 920. In addition, a number of image locations indicated by Xs are shown. A first group 930 of image locations (indicated by Xs) between first end location 820 and beginning point 910, a second group 940 of image locations (indicated by Xs) between beginning point 910 and ending point 920, and a third group 950 (indicated by Xs) between ending point 920 and second end location 830.

Returning to FIG. 6, the image outputs corresponding to the region along the path from the beginning point to the ending point (e.g., the images from image locations between beginning point 910 and ending point 920 of FIG. 9) are aggregated to yield a cumulative image output (block 690). An example graphical representation of such cumulative image output is set forth in as cumulative image output 570 of FIG. 5 discussed above. The cumulative image output is then converted to a graphical representation corresponding to the ending point along the path displayed on a display (block 695). This process may then be repeated with a user selecting different beginning and ending points to yield a different cumulative image. This approach allows a user to generate a number of images across a region of interest, and then aggregate the signal from the multiple images to increase the signal level resulting in an enhanced image. Where ending point 920 or beginning point 910 are set too far, an undesired result such as that exemplified by cumulative image output 575 discussed above in relation to FIG. 5 may result. As an example, image output 505 corresponds to the image output at beginning point 910, image output 520 corresponds to the image output at ending point 920, and image output 530 corresponds to the image output along the path after ending point 920.

In conclusion, the invention provides novel systems, devices, methods and arrangements for structure investigation. While detailed descriptions of one or more embodiments of the invention have been given above, various alternatives, modifications, and equivalents will be apparent to those skilled in the art without varying from the spirit of the invention. For example, while FIG. 6 represents a system and method for material investigation that collects image outputs along a path for a period corresponding to the duration of a pressed button, other embodiments of the present invention may operate without the period of the defined button by collecting a set of image outputs at various increments along the defined path without the limit of a time period. Therefore, the above description should not be taken as limiting the scope of the invention, which is defined by the appended claims.

What is claimed is:

1. An characteristic investigation system for investigating an characteristic of a material, the system comprising:
    an input device operable to designate at least one location on a sample and a time period;
    a beam operable to impinge on the at least one location on the sample for the time period; and
    a detector system operable to repeatedly sense signal data resultant from the interaction of the beam and the sample during the time period, and to generate a first image output corresponding to a first duration of exposure of the at least one location of the sample to the beam and a second image output corresponding to a second duration of exposure of the at least one location of the sample to the beam.

2. The characteristic investigation system of claim 1, the characteristic investigation system further comprising:
    a display system operable to display a graphical representation of a defined region of the sample, wherein the at least one location on the sample is included within the defined region.

3. The characteristic investigation system of claim 2, wherein the detector system is a first detector system, the characteristic investigation system further comprising:
    a second detector system operable to sense a portion of the beam reflected off the sample to yield a third image output from which the graphical representation of the defined region is derived.

4. The characteristic investigation system of claim 3, wherein the second detector system is selected from a group consisting of: a backscatter detector, a forward scatter detector, a secondary electron detector, and a combination of one or more of a backscatter detector, a forward scatter detector, and a secondary electron detector.

5. The characteristic investigation system of claim 3, wherein the first detector system and the second detector system are implemented as the same detector.

6. The characteristic investigation system of claim 2, wherein the graphical representation is a first graphical representation, wherein the display is further operable to display a second graphical representation of the first image output, and to display a third graphical representation of the second image output in place of the first graphical representation at some time after the second graphical representation is available.

7. The characteristic investigation system of claim 6, wherein the display system is further operable to re-display the first graphical representation in place of the second graphical representation.

8. The characteristic investigation system of claim 1, wherein the input device is selected from a group consisting of: a mouse, a touch screen, and a keyboard.

9. The characteristic investigation system of claim 1, wherein the input device includes a button, and wherein the time period corresponds to a period during which the button is pressed.

10. The characteristic investigation system of claim 1, wherein the beam is an electron beam generated by a scanning electron microscope.

11. The characteristic investigation system of claim 1, wherein the detector system is selected from a group consisting of: an X-ray wavelength dispersive spectrometer, an X-ray energy dispersive spectrometer, and an electron backscatter diffraction detector.

12. The characteristic investigation system of claim 1, the characteristic investigation system further comprising:
    a memory operable to store the first image output and the second image output.

13. The characteristic investigation system of claim 1, wherein the second image output is the first image output augmented to include an additional sensed signal data resultant from the interaction of the beam and the sample during a period extending between the end of the first duration and a sample time.

14. The characteristic investigation system of claim 1, wherein the first duration and the second duration are within the time period.

15. The characteristic investigation system of claim 1, wherein the beam is held fixed for both the first duration and the second duration.

16. The characteristic investigation system of claim 1, wherein the beam is moved between the first duration and the second duration.

17. The characteristic investigation system of claim 16, wherein the at least one location includes at least a first location, a second location, a third location, and a fourth location, wherein the beam is moved from the first location to the second location between the first duration and the second duration, and wherein the input device is further operable to designate a beginning point on a path extending from the third location to the fourth location, and an ending point on the path extending from the third location to the fourth location.

18. The characteristic investigation system of claim 17, wherein the first location and the second location are between the beginning point and the ending point, and wherein the characteristic investigation system further comprises:
    a display operable to display a graphical representation of a cumulative image output, wherein the cumulative image output is formed by combining at least the first image output and the second image output.

19. A method for material investigation, the method comprising:
    receiving from an input device a designation of at least one location on a sample, and a time period;
    impinging a beam on the at least one location for the time period; and
    repeatedly sensing signal data resultant from the interaction of the beam and the sample during the time period;
    generating a first image output corresponding to a first duration of exposure of the at least one location of the sample to the beam; and
    generating a second image output corresponding to a second duration of exposure of the at least one location of the sample to the beam.

* * * * *